(12) United States Patent
Fan et al.

(10) Patent No.: US 9,969,984 B2
(45) Date of Patent: May 15, 2018

(54) STORAGE STABLE RECOMBINANT LENTIVIRAL VECTOR PREPARATION

(71) Applicant: BEIJING SOLOBIO GENETECHNOLOGY COMPANY LTD., Beijing (CN)

(72) Inventors: Jundie Fan, Beijing (CN); Lixin Jiang, Beijing (CN); Zhiwen Zhou, Beijing (CN)

(73) Assignee: BEIJING SOLOBIO GENETECHNOLOGY COMPANY LTD., Beijing (CN)

( * ) Notice: Subject to any disclaimer, the term of this patent is extended or adjusted under 35 U.S.C. 154(b) by 146 days.

(21) Appl. No.: 14/386,662

(22) PCT Filed: Mar. 22, 2013

(86) PCT No.: PCT/CN2013/073056
§ 371 (c)(1),
(2) Date: Sep. 19, 2014

(87) PCT Pub. No.: WO2013/139300
PCT Pub. Date: Sep. 26, 2013

(65) Prior Publication Data
US 2015/0056696 A1    Feb. 26, 2015

(30) Foreign Application Priority Data
Mar. 22, 2012  (CN) .......................... 2012 1 0078289

(51) Int. Cl.
*C12N 7/00* (2006.01)

(52) U.S. Cl.
CPC ...... *C12N 7/00* (2013.01); *C12N 2740/15021* (2013.01); *C12N 2740/15043* (2013.01); *C12N 2740/15051* (2013.01); *C12N 2740/16043* (2013.01); *C12N 2740/16051* (2013.01)

(58) Field of Classification Search
CPC .......... C12N 2740/15051; C12N 2740/16051; C12N 2740/15043; C12N 7/00; C12N 2740/16043; C12N 2740/15021
See application file for complete search history.

(56) References Cited

U.S. PATENT DOCUMENTS

| 6,284,469 B1 | 9/2001 | Hope et al. | |
| 7,906,641 B2 | 3/2011 | Zhou et al. | |
| 8,263,761 B2 | 9/2012 | Zhou et al. | |
| 8,283,462 B2 | 10/2012 | Zhou et al. | |
| 8,383,804 B2 | 2/2013 | Zhou et al. | |
| 2005/0186225 A1 | 8/2005 | Evans et al. | |
| 2006/0121055 A1* | 6/2006 | Campbell et al. | 424/209.1 |
| 2006/0171917 A1* | 8/2006 | Campbell et al. | 424/85.1 |
| 2006/0217326 A1 | 9/2006 | Zhou et al. | |
| 2007/0148765 A1* | 6/2007 | Evans et al. | 435/320.1 |
| 2008/0299182 A1* | 12/2008 | Zhang et al. | 424/443 |
| 2009/0233988 A1* | 9/2009 | Miyazaki et al. | 514/44 R |
| 2011/0117188 A1 | 5/2011 | Zhou et al. | |
| 2011/0189264 A1 | 8/2011 | Zhou et al. | |
| 2011/0217361 A1 | 9/2011 | Zhou et al. | |
| 2011/0217362 A1 | 9/2011 | Zhou et al. | |
| 2013/0028933 A1* | 1/2013 | Haynes et al. | 424/210.1 |

FOREIGN PATENT DOCUMENTS

| CN | 1508141 A | 6/2004 |
| CN | 101160139 A | 4/2008 |
| CN | 101657097 A | 2/2010 |
| EP | 1 859 813 A1 | 11/2007 |
| WO | WO2000029024 A3 * | 5/2000 |
| WO | WO 2008/106644 A2 | 9/2008 |
| WO | WO 2008/106646 A2 | 9/2008 |
| WO | WO 2009/056651 A1 | 5/2009 |

OTHER PUBLICATIONS

Ichim et al. "Generation of high-titer viral preparations by concentration using successive rounds of ultracentrifugation." J Transl Med. Aug. 17, 2011;9:137. doi: 10.1186/1479-5876-9-137.*
Croyle et al. "Development of formulations that enhance physical stability of viral vectors for gene therapy." Gene Ther. Sep. 2001;8(17):1281-90.*
Alcock et al. "Long-term thermostabilization of live poxviral and adenoviral vaccine vectors at supraphysiological temperatures in carbohydrate glass." Sci Transl Med. Feb. 17, 2010;2(19):19ra12.*
Bieganski et al. "Stabilization of active recombinant retroviruses in an amorphous dry state with trehalose." Biotechnol Prog. Jul.-Aug. 1998;14(4):615-20.*
Chang et al. "Mechanism of protein stabilization by sugars during freeze-drying and storage: native structure preservation, specific interaction, and/or immobilization in a glassy matrix?" J Pharm Sci. Jul. 2005;94(7):1427-44.*
Nilsson SM . "Process development of lentiviral vector expression, purification and formulation for gene therapy applications." http://discovery.ucl.ac.uk/1485725/1/Nilsson_Thesis_Sara%20Nilsson_21Mar2016_post-corrections.pdf. accessed Apr. 10, 2016.*
Charneau et al., "A Single-Stranded Gap in Human Immunodeficiency Virus Unintegrated Linear DNA Defined by a Central Copy of the Polypurine Tract," *J. Virol* 65(5):2415-2421 (1991).
Frecha et al., "Efficient and stable transduction of resting B lymphocytes and primary chronic lymphocyte leukemia cells using measles virus gp displaying lentiviral vectors," *Blood*, 114(15):3173-80 (2009).
Funke et al., "Targeted Cell Entry of Lentiviral Vectors," *Mol Ther* 16(8):1427-36 (2008).

(Continued)

*Primary Examiner* — Titilayo Moloye
(74) *Attorney, Agent, or Firm* — Leydig, Voit & Mayer, Ltd.

(57) ABSTRACT

Herein is provided a recombinant lentiviral vector preparation, in which the preparation comprises: a) an effective dose of the recombinant lentiviral vector; b) a histidine hydrochloride buffer for keeping a pH value of the preparation in the range of 6.0-8.0; and c) a carbohydrate.

30 Claims, 3 Drawing Sheets

(56) References Cited

OTHER PUBLICATIONS

Goujon et al., "Characterization of Simian Immunodeficiency Virus $SIV_{SM}$/Human Immunodeficiency Virus Type 2 Vpx Function in Human Myeloid Cells," *J Virol* 82(24):12335-45 (2008).

Goujon et al., "With a little help from a friend: increasing HIV transduction of monocyte-derived dendritic cells with virion-like particles of $SIV_{MAC}$," *Gene Ther* 13(12):991-994 (2006).

Mühlebach et al., "Stable Transduction of Primary Human Monocytes by Simian Lentiviral Vector PBj," *Mol Ther* 12(6):1206-16, (2005).

Naviaux et. al., "The pCL vector system: rapid production of helper-free, high-titer, recombinant retroviruses," *J. Virol.* 70(8):5701-5705 (1996).

Rose et al., "Nucleotide sequences of the mRNA's encoding the vesicular stomatitis virus G and M proteins determined from cDNA clones containing the complete coding regions," *J. Virology* 39(2): 519-528 (1981).

Sirven et al., "The human immunodeficiency virus type-1 central DNA flap is a crucial determinant for lentiviral vector nuclear import and gene transduction of human hematopoietic stem cells," *Blood* 96(13):4103-4110 (2000).

Von Gegerfelt et al., "Replacement of Posttranscriptional Regulation in SIVmac239 Generated a Rev-Independent Infectious Virus Able to Propagate in Rhesus Peripheral Blood Mononuclear Cells," *Virology* 232:291-299 (1997).

Wolfrum et al., "Impact of viral accessory proteins of SIVsmmPBj on early steps of infection of quiescent cells," *Virology* 364(2):330-41, (2007).

Zolotukhin et al., "Continuous Propagation of RRE(-) and Rev(-)RRE(-) Human Immunodeficiency Virus Type 1 Molecular Clones Containing a cis-Acting Element of Simian Retrovirus Type 1 in Human Peripheral Blood Lymphocytes," *J Virol.* 68(12):7944-7952 (1994).

State Intellectual Property Office of the People's Republic of China, International Search Report in International Application No. PCT/CN2013/073056 (dated Mar. 22, 2012).

State Intellectual Property Office of the People's Republic of China, Written Opinion in International Application No. PCT/CN2013/073056 (dated Mar. 27, 2013).

International Bureau of WIPO, International Preliminary Report on Patentability in International Application No. PCT/CN2013/073056 (dated Sep. 23, 2014).

State Intellectual Property Office of the People's Republic of China, First Office Action in Chinese Patent Application No. 201210078289.X (dated Jun. 2, 2015).

Barry et al., "Lentivirus Vectors Encoding Both Central Polypurine Tract and Posttranscriptional Regulatory Element Provide Enhanced Transduction and Transgene Expression," *Human Gene Therapy* 12:1103-1108 (2001).

Yang et al., "Inducible, High-Level Production of Infectious Murine Leukemia Retroviral Vector Particles Pseudotyped with Vesicular Stomatitis Virus G Envelope Protein," *Human Gene Therapy* 6:120-1213 (1995).

Zhang et al., "Preparation of Stabilizer of Freeze-dried Adenovirus-based Live HIV Vaccine," *Chin J. Biologicals*, vol. 20. No. 2, pp. 104-106 (2007).

Cruz et al., "Screening of Novel Exipients for Improving the Stability of Retroviral and Adenoviral Vectors," *Biotechnology Progress*, vol. 22, No. 2, pp. 568-576 (2006).

European Patent Office, Extended European Search Report in European Patent Application No. 13 76 4205 (dated Oct. 2, 2015).

\* cited by examiner

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
```

-continued

```
atgcaggccc tggtgctact cc                                               22
```

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2

```
ttagggccc ctggggtcca g                                                 21
```

US 9,969,984 B2

STORAGE STABLE RECOMBINANT LENTIVIRAL VECTOR PREPARATION

CROSS-REFERENCE TO RELATED APPLICATIONS

This application is the U.S. national phase of International Application No. PCT/CN2013/073056 filed on Mar. 22, 2013, which claims priority to Chinese patent application number of 201210078289.X, titled "Recombination lentiviral vector preparation", filed on Mar. 22, 2012 with State Intellectual Property Office of the Republic of China, the content of which is incorporated by reference in this application in its entirety.

INCORPORATION BY REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,096 byte ASCII (Text) file named "718508 ST25.txt", created on Sep. 15, 2015.

FIELD OF THE INVENTION

The invention relates to a viral vector preparation, more particularly to a recombinant lentiviral vector preparation.

BACKGROUND OF THE INVENTION

With the advances on gene therapy technologies, viral vectors are applied more and more in treating human diseases. Among them, lentiviral vectors is the commonly used viral vectors. The lentiviral vector is a reconstructed viral vector system on the basis of HIV-1 virus and can introduce the gene of interest efficiently into animal and human primary cells or cell-lines. The genome of the lentiviral vector which is a plus-strand RNA enters into the cell and is reversely transcribed into DNA in the cytoplasm by a reverse-transcriptase carried by the genome itself to form a DNA pre-integration complex. Then, the complex is transported into the cell nuclei and the DNA is integrated into the cell genome. The integrated DNA is transcribed into mRNAs which are returned to the cytoplasm and expressed into proteins of interest.

The lentiviral vector-mediated gene expression has continuous and stable effect, because the gene of interest has been integrated into a host cell's genome and is divided with the division of the cell genome. Moreover, the lentiviral vector can effectively infect a nondividing cell and can be effectively integrated into the nondividing cell. With the above-mentioned properties, the lentiviral vector has great advantages as compared to the other viral vectors, such as non-integrated adenoviral vector, adeno-associated viral vector with low integration rate, classical retroviral vector which is solely integrated into a dividing cell. Today, tissues or cells where the lentiviral vector-mediated chronic expression of a gene of interest can occur include brain, liver, muscular, retina, hematopoietic stem cells, marrow mesenchymal stem cells, macrophages, etc.

Nevertheless, the stability of the lentiviral vector is very low, while a viral vector which will be used in the therapeutic application of the human body must keep the structural integrity to maintain its biological activity. In order to keep the structural integrity of the viral vector to maintain its biological activity, such preparations must be maintained and delivered at a relatively low temperature.

Loss of biological activities of the lentiviral vector mostly occurs at storage stage. A recombinant lentiviral vector carrying a gene of interest is typically prepared into a liquid preparation and stored at an ultra-low temperature (e.g. no higher than $-60°$ C.), transported under the condition of low temperature and frozen, and thawed before use. It is one of the major challenges that the structural and functional ingredients are prevented from being physically disrupted during freezing and storing at a temperature below freezing point.

Typically, the lentiviral vector preparations comprise proteins encoded by the viral genome and a single- or double-stranded genome. If the virus contains an envelope protein, the preparation further comprises a lipid two-layer membrane. Under a ultra-low temperature, the protein is liable to denaturation and the lipid two-layer membrane is liable to destruction during freezing. Therefore, it is inappropriate for a viral vector preparation to be stored under an ultra-low temperature for a long time.

Furthermore, when the recombinant lentiviral vector is stored at an ultra-low temperature for too long time (e.g., longer than 200 days), when the recombinant lentiviral vector is under freeze-thaw cycles during administration, or when the recombinant lentiviral vector is exposed to the body temperature of an organism (e.g. body temperature of the human being or other animals) or the room temperature too longer time before the preparation reaches the target organ due to improper application, the biological activity of the recombinant lentiviral vector (typically expressed in virus titer) often decreases quickly and dramatically, which directly influences on therapeutic effect of the recombinant lentiviral vector preparation or leads to inaccuracy in results of preclinical or clinical study.

Furthermore, for a clinical setting short of suitable storage apparatuses for viral vectors, the hospital's willingness to adopt the virus preparation depends on the using cost of a virus preparation. Generally, pharmacies and hospitals have freezing apparatuses with the lowest temperature of $-20°$ C., but hardly have freezing apparatuses with the lowest temperature of $-80°$ C. It is always believed that a liquid preparation of a viral vector will be stable only at an ultra-low temperature.

Therefore, there is an urgent need in a recombinant lentiviral vector preparation with good stability. The recombinant lentiviral vector preparation can be stored for a long time under the condition of an ultra-low temperature of $-80°$ C., or can also keep long-term stability under the condition of a middle- or low-temperature of $-20°$ C., or can still be capable of maintaining the activities of the recombinant lentiviral vector which can meet to the requirement in use, after freeze-thaw cycles during administration or after exposure to an organism's body temperature or the room temperature for a longer time.

SUMMARY OF THE INVENTION

Herein is provided a recombinant lentiviral vector preparation, which comprises: a) an effective dose of a recombinant lentiviral vector, b) a histidine hydrochloride buffer for keeping a pH value of the preparation in the range of 6.0-8.0 and c) a carbohydrate.

The recombinant lentivirus preparation in the present invention has a significantly enhanced stability due to containing the certain amount of histidine hydrochloride buffer as the non-conventional ingredient. In particular, it can be stored for a long time under the condition of an ultra-low temperature of −80° C., or can also keep long-term stability under a condition of a middle- or low-temperature of −20° C., or can still be capable of maintaining the activities of the recombinant lentiviral vector which can meet to the requirement in use, after freeze-thaw cycles during administration or after exposure to an organism's body temperature (for example, 37° C.) or the room temperature for a longer time.

DETAILED EMBODIMENTS

Figure 1:
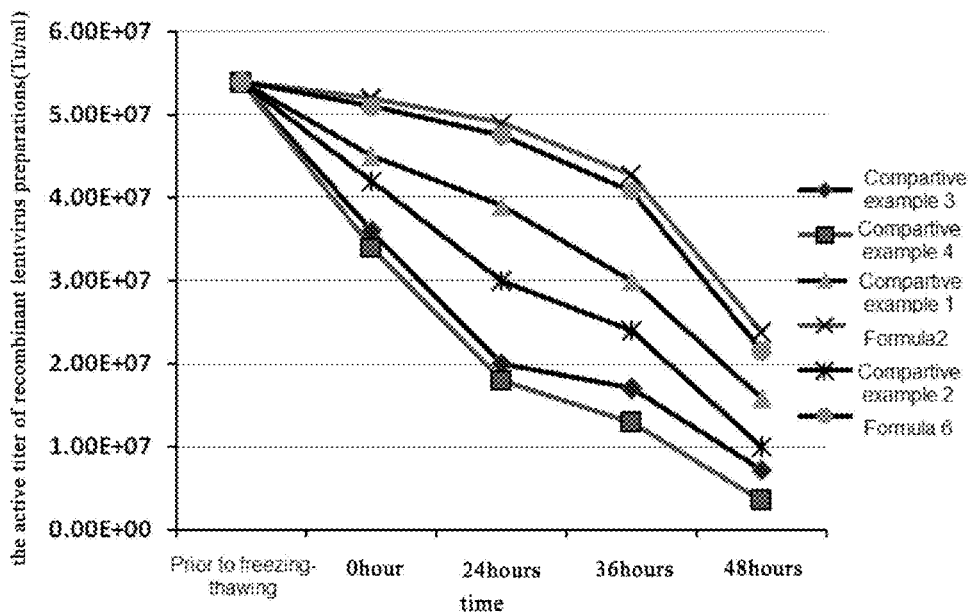
FIG. 1 represents the curves of the stabilities of Formulas 2, 6 and Comparable examples 1-4 at 37° C.

The recombinant lentiviral vector preparation provided in the present invention comprises:
a) an effective dose of the recombination lentiviral vector,
b) a histidine hydrochloride buffer for keeping a pH value of the preparation in the range of 6.0-8.0, and
c) a carbohydrate.

"A viral vector" in the present invention refers to a virus particle which lacks self-replication ability and has a capability of introducing a nucleic acid molecule into a host. "A lentiviral vector" refers to a viral vector derived from a primate immunodeficiency virus. The lentiviral vector comprises genetic information required for packaging, transfection, and stable integration which is the main component of the lentiviral vector system. A lentiviral vector carrying an exogenous genes is packaged into an infectious virus particles via virus packaging with the aid of the lentiviral packaging plasmids and cell-lines. The infectious virus particles infects a cell or a vital tissue to achieve expression of the exogenous gene in the cell or the vital tissue. A "recombinant" viral vector refers to a viral vector constructed by gene recombinant technologies. The recombination viral vector comprises a viral vector constructed by using a DNA encoding the viral genome and a packaging cell.

The recombinant lentiviral vector in the present invention can further be pseudotyped with VSV-G. Pseudotyped with VSV-G refers to the envelope of recombinant lentiviral vector comprises VSV-G protein, a surface glycoprotein of vesicular stomatitis virus (VSV). The VSV-G protein may derive from any one of the VSV strains. For example, without being limited, VSV-G protein from the Indiana serotype strain can be used (J. Virology 39: 519-528 (1981)). Furthermore, VSV-G protein may be a derivative of the naturally occurring protein which is a modified protein obtained by substitution, deletion, and/or addition of one or more amino acids. VSV-G pseudotyped vector can be prepared by co-existing of VSV-G protein with the virus during the production of the virus. For example, a virus particle produced by a packaging cell can be pseudotyped with VSV-G by transfecting the packaging cell with a VSV-G expression vector and inducing to express the VSV-G gene integrated into the host's chromosomal DNA, or by expressing the VSV-G in the packaging cell. The VSV-G protein is a glycoprotein which can form a stable trimmer in the cell membrane, thus the vector particle will not be disrupted during purification and can be concentrated by centrifugation into the vector particle with a high concentration (Yang, Y. et al, Hum Gene Ther: September, 6(9), 1203-13. 1995). Preferably, the recombinant lentiviral vector is a lentiviral vector coated with vesicular stomatitis virus G protein.

The recombinant lentiviral vector in the present invention can further comprise an envelope protein from other viruses. For example, the envelope protein is preferably from a virus which can infect a human cell. The envelope protein includes, but is not limited to, for example the amphotropic retrovirus envelope protein and so on. As the amphotropic retrovirus envelope protein, for example, the envelope protein from murine leukemia virus (MuMLV) 4070A strain can be employed. Additionally, the envelope protein from MuMLV 10A1 can also be used (e.g. pCL-10A1 (Imgenex) (Naviaux, R, K. et. al., J. Virol. 70:5701-5705 (1996)). Furthermore, the examples of the proteins from the family of Herpesviridae include gB of herpes simplex virus, gD of herpes simplex virus, gH of herpes simplex virus, gp85 of herpes simplex virus, gp350 of EB virus and gp220 of EB virus, etc. the examples of the proteins from the family of Hepadnaviruses include S protein of Hepatitis B virus and so forth. The envelope protein can also be formed by fusion of a glycoprotein of measles virus and other single-chain antibodies (Funke S. et al., Mol Ther 16:1427-36, 2008; Frecha C. et al., Blood, 114:3173-80, 2009).

A lentiviral vector is generally packaged by transient transfection or packaging with cell lines. For example, the human cell strain used as a packaging cell in the transient transfection includes 293 cell, 293T cell, 293FT cell, 293LTV cell, 293EBNA cell and other clones isolated from 293 Cell; SW480 cell, u87MG cell, HOS cell, C8166 cell, MT-4 cell, Molt-4 cell, HeLa cell, HT1080 cell, and TE671 cell, etc. The simian cell strain used as a packaging cell is, for example, COS1 cell, COS7 cell, CV-1 cell, BMT10 cell and the like. Moreover, calcium phosphate and PEI are commonly used as transfection reagents, and some other transfection reagents such as Lipofectamine 2000, FuGENE and S93 fectin are often used.

Some lentiviral packaging cell lines, e.g. the most commonly used stable cell-lines generated with Env glycoprotein, VSVG protein or HIV-1 gag-pol protein, are also used in packaging a lentivirus.

For safety, the lentiviral vector system is used on large scale in the form of separated genomes, i.e., genes with different accessory functions are localized in different plasmids. Currently, there are a four plasmid system (where the gag-pol gene, Rev gene, VSVG gene, and SIN transfer gene are located in four different plasmids respectively), a three plasmid system (where the gene encoding for Rev is removed and the gag-pol gene of the gag-pol plasmid uses preferred codons in a human cell) and a two plasmid system (where the accessory genes essential for packaging of lentiviral vector are located in the same plasmid and these accessory genes are the single-copy gene sequence, and the other plasmid is a transgenic plasmid). Also, systems comprising more than four plasmids are in use.

The recombinant lentiviral vector preparation mentioned in the present invention can essentially be completely purified. The purification methods comprise using known purification/separation processes, such as filtration with a filter, ion exchange chromatography, ultra-filtration, molecular sieve, nuclease digestion, and filter sterilization. Generally, a high speed centrifugal process is also used on small-scale preparation. For example, the vector can be deposited and concentrated by filtration of the vector suspension with a 0.45 μm filter and centrifugation at 4° C. at 4,2500×g for 90 min.

Preferably, the recombinant lentiviral vector is a primate recombinant lentiviral vector, i.e., a recombinant human immunodeficiency virus vector (HIV), a recombinant simian immunodeficiency virus vector (SIV), or a non-primate recombinant lentiviral vector, i.e., a recombinant equine infectious anemia virus (EIVA), a recombinant feline immunodeficiency virus (FIV), or a recombinant caprine arthritis-encephalitis virus (CAEV).

Preferably, the recombinant lentiviral vector is a recombinant human immunodeficiency virus vector or a recombinant simian immunodeficiency virus vector. A "simian immunodeficiency virus (SIV) vector" mentioned in the present invention refers to a vector in which the sequences essential for the functions of the viral vector are those derived from SIV genome. "The sequences essential for the functions of the viral vector" in the present invention refer to the sequences of the R region of 5'LTR, U5 region, the packaging signal (φ), RRE, the U3 and R regions excluding the promoter region of 3'LTR by starting from the 5' terminus in sequence. A SIV vector in the present invention can also be modified, so long as it falls within the above-mentioned definition. For example, other sequences derived from SIV or non-SIV can also be comprised in the vector, so long as "the sequences essential for the functions of the viral vector" is derived from SIV. With respect to the most appropriate sequence that can be comprised in the vector, it may be cPPT (central polypurine tract), internal promoter (CMV), or woodchuck hepatitis virus post-transcriptional regulatory element (WPRE).

In the present invention, the simian immunodeficiency virus includes all SIV strains and sub-types thereof. Examples of an isolated SIV strain include, but is not limited to, SIVagm, SIVcpz, SIVmac, SIVmnd, SIVsm, SIVsnm, and SIVsyk, etc.

"A human immunodeficiency virus (HIV) vector" in the present invention refers to a vector in which the sequences essential for the functions of the viral vector are those derived from HIV genome. Among them, the HIV-1 vector contains HIV cis-acting sequences required for packaging, reverse transcription and integration and has a multi-cloning site under the control of a heterologous promoter and a gene of interest inserted at the site. The HIV-1 cis-acting sequences on the vector plasmid typically comprise the LTRs at both ends, a splicing site, and the packaging signal LP, etc. A HIV vector in the present invention can also be modified, so long as it falls within the above-mentioned definition. For example, other sequences derived from HIV or non-HIV can also be comprised in the vector, so long as "the sequences essential for the functions of the viral vector" is derived from HIV. With respect to the most appropriate sequence that can be comprised in the vector, it may be cPPT (central polypurine tract), internal promoter (CMV), woodchuck hepatitis virus post-transcriptional regulatory element (WPRE).

In the present invention, the human immunodeficiency virus includes all HIV strains and sub-types thereof. HIV includes two types of viral strains: HIV-1 and HIV-2. HIV-1 is divided into M, O, N sub-type groups. M sub-type group includes sub-types A, A2, B, C, D, E, F1, F2, G, H, J, K, while O and N sub-types is scarcely seen. HIV-2 includes A, B, C, D, E, F, G sub-types. HIV-2 has biological properties similar to those of HIV-1, but has less virulence.

The recombinant lentiviral vector can be a SIV or HIV vector carrying any gene of interest. Preferably, the recombinant lentiviral vector is any one of the following virus vectors: a recombinant simian immunodeficiency virus vector carrying the human pigment epithelium-derived factor gene, a recombinant human immunodeficiency virus vector carrying the human pigment epithelium-derived factor gene, a recombinant simian immunodeficiency virus vector carrying small RNA fragments interfering with the replication of HIV virus, and a recombinant human immunodeficiency virus vector carrying small RNA fragments interfering with the replication of HIV virus.

The recombinant lentiviral vector can be a recombinant simian immunodeficiency virus vector or a recombinant human immunodeficiency virus vector carrying gene of epidermal growth factor EGF, fibroblast growth factor FGF2, ciliary neurotrophic factor CNTF, GDNF, BDNF, LEDGF, EPO, NT-3, NT-4, and/or RdCVF, etc.

Pigment epithelium-derived factor (PEDF), is a member of the serine protease superfamily, which has highly conserved sequence and unique molecular structure. PEDF is becoming a hotspot in the studies due to possessing a variety of functions such as nerve nutrition, suppression of neovascularization, anti-tumor, etc. Function of PEDF in suppression of neovascularization is particularly important. PEDF plays a key role in retinitis pigmentosa, retinal detachment, retina ischemic disorder. The lentiviral vectors provide a particularly suitable way for drug delivery because they enable introduced exogenous genes to be integrated stably into the chromosome in the dividing cells and to allow persistent expression in the host.

A recombinant simian immunodeficiency virus vector carrying the pigment epithelium-derived factor gene of the present invention (SIV-PEDF vector) refers to a recombination SIV vector carrying a PEDF gene. The SIV-PEDF vector of the present invention is independent of species or structures, so long as it falls within the above-mentioned definition. The SIV-PEDF vector can be a SIV-PEDF vector having any one of base sequences mentioned in Pat. Appl. No. 200680012882.7.

A recombinant human immunodeficiency virus vector carrying the pigment epithelium-derived factor gene of the present invention (HIV-PEDF vector) refers to a recombination HIV vector carrying a PEDF gene.

Preferably, the recombinant lentiviral vector is a recombinant simian immunodeficiency virus vector or a recombinant human immunodeficiency virus vector carrying small RNA fragments interfering with the replication of HIV virus. The small RNA fragments interfering with the replication of HIV virus (abbreviated herein as siHIV) may be selected from one or more of SEQ ID Nos. 1-9 mentioned in ZL02156785.9.

Preferably, the recombinant lentiviral vector carries some single-copy genes, e.g. RPE65 and the like. Mutation and deletion in these genes typically lead to some hereditary diseases. A better therapeutic effect will be attained by re-infusing the particular stem cells, which is infected with the lentiviral vector carrying some correct genes, into the patient's body.

Preferably, the recombinant lentiviral vector also carries the central polypurine tract and/or the post-transcriptional regulatory element of woodchuck hepatitis virus. Furthermore, the gene transfer vector DNA has better be modified to increase the efficiency in introduction and expression of PEDF gene. The examples of increasing the efficiency in introduction include the HIV vectors or SIV vectors into which cPPT, WPRE, constitutive transport element CTE, RNA transport element RTE or accessory gene Vpx from HIV-1 virus can be introduced.

Among the sequences, cPPT is a sequence originally present in the SIV genome. In the HIV virus, cPPT had been noted long before in a report (P. Charneau et al., J. Virol 65:2415-2431, 1991) that the efficiency in gene introduction is increased because the transfer of the vector genome into the cell nucleus is accelerated after introducing the cPPT into a HIV vector (A. Sirven et al., Blood 96: 4103-4110, 2000). WPRE is a factor having a function of increasing the efficiency of gene expression (U.S. Pat. No. 6,284,469: RNA export element and methods of use). It had been reported that introduction of both factors of cPPT and WPRE into other lentiviral vectors can further increase the effects of each other (SC. Barry et al., Hum. Gene Ther. 12:1103-1108, 2001).

In the SIV vector carrying a PEDF gene of the present invention, cPPT can be localized in the same manner as that in a typical lentiviral vector. For example, cPPT can be localized between the promoter and the exogenous gene, or at upstream of the RRE sequence, preferably at upstream of the above-mentioned non-LTR promoter driving transcription of the carried gene. WPRE can be localized at downstream of the carried gene of interest such as PEDF or FGF2 gene.

Said recombinant lentiviral vector also carries accessory gene Vpx. The accessory gene Vpx helps increasing the transduction efficiency for myeloid cells, such as monocytes, macrophages, dendritic cells, etc. (Goujon C. et al., Gene Ther 13:991-994 (2006); Goujon C. et al., J Virol 82:12335-45 (2008); Muhlebach M. D. et al., Mol Ther 12:1206-16, (2005); Wolfrum N. et al., Virology 364:330-41, (2007)).

The recombinant lentiviral vector also carries the CTE sequence capable of replacing the REV and RRE sequences (von Gegerfelt A. S. and Felber B. K., Virology 232:291-299, 1997; Zolotukhin A. S. et al., J Virol. 68:7944-7952).

The dosage of the recombinant lentiviral vector is $2\times10^6$-$2\times10^{10}$ transducing unit/milliliter (Tu/ml). The dosage of the recombinant lentiviral vector is $5\times10^6$-$2\times10^{10}$ Tu/ml. Preferably, the dosage of the recombinant lentiviral vector is $5\times10^6$-$5\times10^8$ Tu/ml, and the preferred dosage is $5\times10^6$-$2\times10^7$ Tu/ml.

The pH value of the preparation is in the range of 6.5-7.4. The pH value of the preparation is 7.2.

The molar concentration of histidine hydrochloride is in the range of 1-50 mmol/L. The molar concentration of histidine hydrochloride is in the range of 10-50 mmol/L. The molar concentration of histidine hydrochloride is 10 mmol/L.

The carbohydrate is at least one selected from a monosaccharide and a non-reducing disaccharide. It is more preferable that the carbohydrate is at least one selected from glucose, fructose, trehalose and sucrose. Percent weight in volume for the carbohydrate is in the range of 2-10% (w/v), on the basis of the recombinant lentiviral vector preparation. It is more preferable that percent weight in volume for the carbohydrate is in the range of 5-10% (w/v), on the basis of the recombinant lentiviral vector preparation. It is most preferable that percent weight in volume for the carbohydrate is 10% (w/v) or 5% (w/v), on the basis of the recombinant lentiviral vector preparation.

The recombinant lentiviral vector preparation comprises:
a) the recombinant simian immunodeficiency virus vector carrying the human pigment epithelium-derived factor gene at a dosage of $2\times10^6$-$2\times10^{10}$ Tu/ml;
b) 10 mmol/L of the histidine hydrochloride buffer for keeping the pH value of said preparation in the range of 7.2; and
c) trehalose at a concentration of 10% by percent weight in volume (w/v) on the basis of the recombinant lentiviral vector preparation.

Wherein the dosage of component a) in the recombinant lentiviral vector preparation is preferably $5\times10^6$-$5\times10^8$ Tu/ml, more preferably $5\times10^7$-$5\times10^8$ (Tu/ml).

The recombinant lentiviral vector preparation comprises:
a) a recombinant simian immunodeficiency virus vector carrying the human pigment epithelium-derived factor gene at a dosage of $2\times10^6$-$2\times10^{10}$ Tu/ml;
b) 10 mmol/L of a histidine hydrochloride buffer for keeping the pH value of said preparation in the range of 7.2; and
c) glucose at a concentration of 5% by percent weight in volume (w/v) on the basis of the recombinant lentiviral vector preparation.

wherein the dosage of component a) in the recombinant lentiviral vector preparation is preferably $5\times10^6$-$5\times10^8$ Tu/ml, more preferably $5\times10^7$-$5\times10^8$ Tu/ml.

The recombinant lentiviral vector preparation further comprises an isosmotic agent. The NaCl isosmotic equivalent of the isosmotic agent corresponds to 0.6%-2.7% of sodium chloride solution. The osmolality tolerable for the eye corresponds to 0.6%-2% of sodium chloride solution; 0.45%-2.7% of sodium chloride solution is tolerable for intra-muscular injection; the osmolality specified in the Chinese Pharmacopoeia is 0.9-1.1, corresponding to 0.8%-1.1% of sodium chloride solution; the osmolality of the serum is typically about 285 mosm/kg and varies in the range of approximately 275-300 mosm/L corresponding to 0.83%-0.91% of NaCl solution. The isosmotic agent is NaCl. Keeping the recombinant lentiviral vector under isosmotic concentrations is advantageous for long-term storage of the virus preparations and for avoiding disintegration of the viral vector due to the low osmotic pressure; on the other hand, the isosmotic virus preparation can be delivered into human body in a painless or substantial painless way and is easy to be assimilated by the human body.

The recombinant lentiviral vector preparation further comprises 2 mmol/L $MgCl_2$.

The recombinant lentiviral vector preparation further comprises a surface-active agent at a concentration of 0.005-0.015% by percent weight in volume (w/v), on the basis of the recombinant lentiviral vector preparation. The surface-active agent is at least one selected from of Tween-20, Tween-80, and polyoxyethylene hydrogenated castor oil RH-40.

The recombinant lentiviral vector preparation further comprises a preserving agent at a final concentration of 0.001-1.0% by percent weight in volume, on the basis of the recombinant lentiviral vector preparation. The preserving agent is phenol at a concentration of 0.5-1.0% by percent weight in volume (w/v), on the basis of aqueous solution of phenol.

The recombinant lentiviral vector preparation further comprises mannitol. The content of mannitol is 0.5-30% by volume, preferably 5-25%, on the basis of the recombinant lentiviral vector preparation. The major role of mannitol in the preparation is to prevent effectively proteins from denaturation and protect the viral coat proteins from deactivation when the preparation is stored at a low temperature. On the other hand, if the preparation is to be formulated into a lyophilized dosage form, mannitol acts as a skeleton, favorable for shaping as well as accelerating redissolution; if the preparations is to be formulated into a tablet, mannitol as a excipient provides the performance including no hygroscopicity, rapid desiccation, good stability, excellent palatability, and good granulating property for the tablet.

The recombinant lentiviral vector preparation further comprises glycerol. The content of glycerol is 5-30% by volume, preferably 10-30%, on the basis of the recombinant lentiviral vector preparation. Since glycerol has three alcoholic hydroxyl groups and superior water-solubility, it can increase the stability of the lentiviral vector preparation in the histidine hydrochloride buffer. Moreover, glycerol has a certain degree of amphiphilicity to form a protective layer for the amino acid residues on the lentiviral vector envelope protein, thus increasing the stability of the lentiviral vector to some degree. Furthermore, glycerol as an isosmotic adjusting agent, a winterizing agent, a taste-masking agent is a safest excipient and favorable for shaping of the lentiviral vector preparation by freeze-drying if the preparation is to be formulated into a lyophilized dosage form.

Said recombinant lentiviral vector preparation further comprises human serum albumin and/or bovine serum albumin. Percent weight in volume for the albumin is 0.5-5%, preferably 1-3%, on the basis of the recombinant lentiviral vector preparation. Human serum albumin has affinity for the envelope glycoprotein of the lentiviral vector, in particular for VSVG envelope protein, therefor increasing the stability of the lentiviral vector preparation.

The recombinant lentiviral vector preparation further comprises at least one of histidine, glycine, alanine and lysine. Preferably, 0.1 mM-10 mM of histidine is comprised. Amino acids can increase tension between the envelope protein of the lentiviral vector, especially the VSVG envelope protein and histidine hydrochloride buffer, and therefor increase the degree of hydration of the envelope protein of the lentiviral vector, so that the stability of the preparation is enhanced. When the preparation is to be formulated into a lyophilized dosage form, higher viral activities will be maintained due to amino acids which increase the degree of hydration of the envelope protein of the lentiviral vector and alleviate the damage of mechanic shear to the envelope protein to facilitate crystallization of the lentiviral vector and to reduce aggregation of the lentiviral vector during lyophilization.

The recombinant lentiviral vector preparation further comprises an antioxidant at a concentration of 0.01-1.0% by percent weight in volume (w/v), on the basis of the recombinant lentiviral vector preparation. The antioxidant is sodium sulfite or sodium bisulphite at a concentration of 0.1-0.2% by percent weight in volume (w/v), on the basis of the recombinant lentiviral vector preparation, or sodium thiosulfate at a concentration of 0.1% by percent weight in volume (w/v), on the basis of the recombinant lentiviral vector preparation.

The recombinant lentiviral vector preparation further comprises dimethyl sulfoxide (DMSO) at a concentration of 5-50% or polyprene at a concentration of 2-20% by percent weight in volume, on the basis of the recombinant lentiviral vector preparation. DMSO or polyprene can increase the infection efficiency and the stability of the preparation.

The recombinant lentiviral vector preparation further comprises the cytokines required for growth of hematopoietic stem cells or peripheral blood monocytes, at a concentration of 5-10% by percent weight in volume on the basis of the recombinant lentiviral vector preparation. These cytokines increase the concentration and the stability of the preparations. For example, the cytokines are granulocyte colony stimulating factor, IL-3, IL-7, IL-11, SCF, G-SCF, GM-SCF and the like.

when a recombinant lentiviral vector preparation in the present invention is administered by injection or when non-biocompatible ingredients of recombinant lentiviral vector in the present invention have been removed according to the subject's condition in vivo, the injection dose can be common one in the field, up to 300 microliters, typically 1-200 microliters, preferably 50-150 microliters; if the preparation is injected into the subretinal space in human being, a single injection dosage for each of the eyes is 50-150 microliters, preferably 100 microliter. The effective dosage administered to a human subject is typically $2 \times 10^6$-$2 \times 10^{10}$ Tu/individual.

The present invention will be further illustrated in combination with the following examples. The reagents and culture media used in the present invention are commercially available products unless specifically specified.

PREPARATION EXAMPLE

Preparation Example 1. Preparation of a SIV Lentiviral Vector Carrying PEDF and Determination of Titer Thereof 1. Preparation of a SIV Lentiviral Vector Carrying PEDF a SIV gene transfer vector, a packaging vector, a rev expression vector, and a VSV-G expression vector were obtained with reference to the method in the patent CN200680012882 and the hPEDF fragment is introduced into the gene transfer vector. Among them, the obtained gene transfer vectors include three types, ie., a gene transfer vector with the cPPT fragment alone, a gene transfer vector with the WPRE fragment alone and a gene transfer vector with both cPPT and WPRE fragments.

The cell line 293T cells derived from human fetal kidney cells were seeded at a cell density of approximate $1 \times 10^7$ cell per plastic Petri dish having the diameter of 15 cm (cell density of 70-80% next day) and cultured in 20 ml of D-MEM culture medium (Gibco BRL) supplemented with 10% fetal bovine serum for 24 hrs. After 24 h of cultivation, the culture medium was replaced with 10 ml of OPTI-MEM culture medium (Gibco BRL), as transfected cells, it is ready for use.

For one petri dish, 10 µg of the gene transfer vector, 5 µg of the packaging vector, 2 µg of the rev expression vector and 2 µg of VSV-G expression vector were dissolved in 1.5 ml of OPTI-MEM medium, and 40 µl of PLUS Reagent reagent (Invitro Co.) was added. The resulting mixture was stirred and left at room temperature for 15 min. Adding the dilute solution which was obtain by diluting 60 µl of LIPOFECT AMINE Reagent with 1.5 ml of OPTI-MEM medium was added, the resulting mixture was stirred and left at room temperature for 15 min. The resulting DNA-complex was dropped onto the cells in the above-described Petri dish having the diameter of 15 cm. The Petri dish was shook carefully to achieve uniform mixing, and then incubated in a incubator at 37° C., 5% $CO_2$ for 3 hrs. 13 ml of D-MEM medium comprising 20% of fetal bovine serum was added into the above-mentioned petri dish and cultured.

Next day after transfection, the D-MEM medium was replaced with 30 ml of a fresh DMEM medium containing 10% of fetal bovine serum. Two days after transfection, the supernatant was recovered and 20 ml of the fresh medium was added. The recovered supernatant was filtered with a 0.45 µm filter and stored at 4° C. Three days after transfection, the supernatant was recovered, filtered with a 0.45 μm filter and mixed with the recovered supernatant the day before. The mixture was concentrated with a high-speed centrifuge. The recovered suspensions were aliquoted among sterilized test tubes, and then centrifuged at 4° C. at 4,2500 g for 1 h. The centrifugation procedure was repeated twice to concentrate the vector suspension by 500-1000 times. The vector was deposited as a deposition and the deposition was dissolved with D-PBS. The concentrated vector was subjected to column chromatography (GE Healthcare, XK16/100, filler 4FF (Sepharose 4 Fast Flow), injection rate: 1.5 ml/min, bed height: 90 cm) and the first peak was collected. The collected samples were filtered with a 0.22 μm filtration membrane and were aliquoted. A few of aliquots were used in titer determination, the others were stored at −80° C. until use.

2. Titer Determination

The titer of the lentiviral vector includes a functional titer calculated by the number of the cells expressing the protein of the carried gene (Functional titer: TU/ml). The HEK293T cells were seeded at a certain density ($2\times10^5$/well) in a 24-well plate (BD company) and 0.5 ml of the mixture of the cell with D-MEM medium (Gibco BRL) containing 10% fetal bovine serum was added to each of wells. The 24-well plate was placed and cultured in a $CO_2$ incubator at 37° C. for 24 h. The stock solution of the virus carrying both cPPT and WPRE fragments prepared as above and the negative control D-PBS were diluted with OPTI-MEM medium respectively. The 10-fold serial dilutions of the virus solution were marked as Dilution 1 ($\frac{1}{10}$ of the original concentration), Dilution 2 ($\frac{1}{10^2}$ of the original concentration), Dilution 3 ($\frac{1}{10^3}$ of the original concentration), Dilution 4 ($\frac{1}{10^4}$ of the original concentration), and Dilution 5 ($\frac{1}{10^5}$ of the original concentration) respectively. The 10-fold serial dilutions of the negative control were marked as Negative control 1-5 for use.

Cells were rinsed with 0.5 ml/well of OPTI-MEM (Gibco BRL), with gentle manipulation for avoiding cell detachment. The diluted virus solution and the diluted negative control mentioned above were subsequently added to HEK293T cells, and the diluted virus solution and the negative control at different concentration are respectively in triplicates (200 μL/well). The corresponding signs are marked clearly. The 24-well plates with the infective virus solution were placed and cultured in a $CO_2$ incubator at 37° C. for cultivation. After 24 hrs, the plates were supplemented with a DMEM medium containing 20% fetal bovine serum (200 μL/well). The plates were placed and cultured in a $CO_2$ incubator at 37° C. for 24 hrs.

Subsequently, a immunofluorescence detection was performed. Specifically, the supernatants were pipetted and discarded. The plates were rinsed with 500 μl/well of D-PBS stored at 4° C. once. The D-PBS was pipetted and discarded. 500 μL/well of cooled absolute ethanol (−30° C.) was added and left at 4° C. for 10 min. The absolute ethanol was pipetted and discarded. The plate were dried at room temperature for 5 min. The cells were rinsed with 500 μl/well of D-PBS of room temperature and 100 μl/well of a primary antibody is added (Human Serpin F1/PEDF specific polyclonal goat IgG, R&D, Cat. No. AF1177, 1.5 μg/ml). The plates were placed in an incubator at 37° C. for 1 h, with shaking once every 15 min. The primary antibody was pipetted and discarded, the cells were rinsed twice with 500 μl/well of D-PBS of room temperature. The D-PBS was pipetted and discarded and 200 μl/well of a secondary antibody was added (Alexa Flour 488 Rabbit Anti-goat IgG, Invitrogen, Cat. No. A-11078). The plates were then placed in the dark in the incubator at 37° C. for 1 h with shaking once every 15 min. The cells were rinsed twice with 500 μl/well of D-PBS of room temperature and 300 μl/well of D-PBS of room temperature (Dulbecco's Phosphate-Buffered Saline) was added. The plates were then placed at 4° C.

Counting: the plates were observed with the 20× lens of a fluorescence microscope. The virus solution with the number of the fluorescent cells between 20 and 80 per visual field were selected as a sample, and the sample was photographed in the mode of selecting six points per well according to a pentagram format, i.e. five apexes of the pentagram and the central point of the pentagram for counting.

The titer of the virus solution was calculate according to the following formula: titer of the virus solution (TU/ml)= the number of the fluorescent cells per visual field×dilution factor×345.36.

It was known from the above calculation that the titer of the virus solution was $2\times10^{10}$ TU/ml wherein the virus solution is obtained through the expression vector carrying both cPPT and WPRE fragments constructed in the Preparation Example 1.

According to the same method as the above, the titers of the virus solutions obtained through the expression vectors carrying cPPT fragment alone were determined to be $1\times10^8$ TU/ml, and the titers of the virus solutions obtained through the expression vectors carrying WPRE fragment alone were determined to be $3\times10^8$ TU/ml.

Preparation examples of the lentiviral vector preparation include, but are not limited to, the viral vector carrying both cPPT and WPRE fragments. The following lentiviral vector preparations can be any viral vector obtained by equivalent replacement or modification for the viral vector in the present invention.

Preparation Example 2. Preparation of a HIV Lentiviral Vector Carrying PEDF and Determination of Titer Thereof 2-1. Construction of the Recombination Lentivirus Gene Transfer Vector HIV-hPEDF The hPEDF CDS fragment was PCR amplified from cDNA of the human Retinal pigment epithelium cell strain ARPE-19 (purchased from American type culture collection, ATCC) as a template using the following primers:

```
                                                (SEQ ID NO: 1)
hPEDF-Forword (forward primer):
atgcaggccctggtgctactcc;

(SEQ ID NO: 2)
hPEDF-Reverse (reverse primer):
ttaggggcccctggggtccag.
```

Cycling conditions for the PCR reaction were as follows: denaturation at 95° C. for 5 min, 40 cycles of 95° C., 30 s; 60° C., 1 min; 72° C., 45 s, final elongation at 72° C. for 10 min.

The hPEDF fragment obtained by gel recovery was ligated into the pLenti6.3/V5-TOPO® vector (Invitrogen) by TA cloning procedure following the manufacturer's instruction. The sequence of the ligated hPEDF fragment was verified by sequencing.

2-2. Large-Scale Preparation of the HIV Lentiviral Vector Carrying the hPEDF Sequence The HIV lentiviral vector carrying the hPEDF sequence was prepared on large-scale according to the method in the Preparation Example 1 and the titer of the HIV lentiviral vector was determined. The titer of the virus solution of HIV lentiviral vector carrying the hPEDF sequence was determined to be $2\times10^{10}$ TU/ml.

Preparation Example 3. Preparation of the Lentiviral Vector Preparation (1) Preparation of the Lentiviral Vector Preparation of Formula 2

1. Preparing a preservation solution for the lentiviral vector: 150 ml of 10 mM histidine hydrochloride buffer was measured, 20 g of trehalose was added, the resulting mixture was stirred to mix well, and diluted with 10 mM histidine hydrochloride to 200 ml and the pH is adjusted to 7.2 for use.

2. Formulation of the Preparation of Formula 2

$2\times10^{10}$ TU/ml of the viral vector obtained in the Preparation Example 2 was diluted with D-PBS to $5.4\times10^7$ Tu/ml, 1 ml of the dilution was pipetted into a labelled ultra-filtration tube and diluted with the above-mentioned preservation solution to 15 ml. After centrifugation at 4° C., 3000 rpm/min for 2-3 min, the supernatant was discarded and 3 ml of the remaining liquid was retained. The retained liquid was diluted with the above-mentioned preservation solution to 15 ml again and re-centrifuged one time at 3000 rpm/min. The final volume of the recombinant lentiviral vector preparation was restricted to be 1 ml.

The preparation was filtered through a 0.22 μm filtration membrane and aliquoted sterilely. Any one of the aliquots was titered immediately (within 20 min). All of the above experimental steps were performed on ice at 0° C. The remaining aliquots were flash frozen in liquid nitrogen and then directly stored at −80° C.

3. Determination of the Titer of the Preparation of Formula 2.

Methods for titer determination is the same as that in Preparation Example 2 and the viral titer of the preparation was determined to be $5.4\times10^7$ TU/ml. It shows that the viral titer of the preparation hardly decreases using this method.

(2) Preparation of the Other Formulas in Table 1 and the Comparable Examples in Table 2

The other formulas in Table 1 and the Comparable examples in Table 2 were prepared using the same procedure as in section (1), i.e., the ingredients except the buffer in the formulas were added to the buffer and mixed well. The mixture was diluted to a certain volume. The pH value was adjust to prepare the preservation solution for the viral vector. Then, the preservation solution was substituted for D-PBS to prepare the preparation.

TABLE 1

Formula of the recombinant lentiviral vector preparation of the present invention

| Formula number | lentiviral vector (Tu/ml) | histidine hydrochloride (mM) | stabilizing agent (w/v) | others | pH value | surface-active agent (w/v) | preservative agent (w/v) | anti-oxidant (w/v) |
|---|---|---|---|---|---|---|---|---|
| 1 | $2\times10^{10}$ SIV-hPEDF | 1 | 5% trehalose | | 6.0 | | | |
| 2 | $5.4\times10^7$ SIV-hPEDF | 10 | 10% trehalose | | 7.2 | | | |
| 3 | $2\times10^6$ SIV-hPEDF | 50 | 7% trehalose | | 7.4 | | | |
| 4 | $5\times10^6$ SIV-hPEDF | 1 | 2% glucose | | 8.0 | | | |
| 5 | $2\times10^6$ SIV-hPEDF | 25 | 3% trehalose + 4% glucose | | 6.5 | | | |
| 6 | $5.4\times10^7$ SIV-hPEDF | 10 | 5% glucose | | 7.2 | | | |
| 7 | $5\times10^8$ SIV-hPEDF | 10 | 5% sucrose | 2 mM MgCl$_2$ | 7.2 | | | |
| 8 | $5\times10^6$ SIV-hPEDF | 10 | 10% fructose | 2 mM MgCl$_2$ | 7.2 | 0.01% Tween-80 | | |
| 9 | $5.4\times10^7$ SIV-siHIV | 50 | 10% trehalose | 5% (w/v) mannitol | 7.2 | 0.015% Tween-20 | | |
| 10 | $5\times10^6$ SIV-siHIV | 10 | 3% trehalose + 5% glucose + 2% sucrose | 1% human serum albumin | 7.4 | | phenol 0.5% | |
| 11 | $2\times10^6$ HIV-hPEDF | 10 | 10% trehalose | 1% glycine | 7.2 | 0.005% Tween-80 | phenol 1.0% | sodium sulfite 0.1% |
| 12 | $5\times10^6$ HIV-hPEDF | 10 | 5% glucose | 20% dimethyl sulfoxide | 7.2 | | | sodium sulfite 0.2% |
| 13 | $5\times10^6$ HIV-hPEDF | 10 | 5% glucose | 5% SCF | 7.2 | | phenol 1.0% | sodium sulfite 0.2% |

Keeping the recombinant lentiviral vector under isosmotic condition is advantageous for long-term storage of the virus preparations and avoiding disintegration of the viral vector due to the low osmotic pressure, while the isosmotic virus preparation can be delivered in a painless or substantial painless way into human body and easy to be assimilated by the human body. In order to investigate the stability of the above-mentioned formulas, the above-mentioned recombinant lentiviral vector preparations of Formulas 4, 8, and 10 were randomly selected and adjusted with NaCl as the isosmotic agent to NaCl isosmotic equivalent of 0.6%-2.7% of sodium chloride solution.

TABLE 2

Comparable Examples of the recombinant lentiviral vector preparation

| Comparable example 1 | a. SIV-hPEDF of $5.4 \times 10^7$ Tu/ml<br>b. 10 mM hydroxymethyl aminomethane Tris<br>c. 10% trehalose (w/v)<br>d. 2 mM $MgCl_2$<br>e. 0.01% Tween-80<br>f. pH 7.2 |
|---|---|
| Comparable example 2 | a. $5.4 \times 10^7$ Tu/ml SIV-hPEDF<br>b. D-PBS<br>c. 10% trehalose (w/v)<br>d. 0.01% Tween-80<br>e. pH 7.2 |
| Comparable example 3 | a. $5.4 \times 10^7$ Tu/ml SIV-hPEDF<br>b. 10 mM Tris<br>c. 5% glucose (w/v)<br>d. 2 mM $MgCl_2$<br>e. 0.01% Tween-80<br>f. pH 7.2 |
| Comparable example 4 | a. $5.4 \times 10^7$ Tu/ml SIV-hPEDF<br>b. D-PBS<br>c. 2.5% or 5% glucose (w/v)<br>e. 0.01% Tween-80<br>f. pH 7.2 |

Effect Testing Example: The Active Titer Determination of Recombinant Lentivirus Preparations at Different Temperatures (1) Effect of Different Recombinant Lentiviral Vector Preparations on the Stability of the Recombination Lentivirus at 37° C.

The recombinant lentiviral vector preparations prepared in Examples 1-13 and Comparable examples 1-4 were taken out from the storage circumstance of −80° C. and immediately placed into a water bath of 37° C. The corresponding samples were placed at different time points (48 h, 36 h, 24 h, 0 h). All of the samples was subjected to the active titer determination at the same time. The Determination titer of the viral particles was performed according to the method in the preparation examples. The results were shown in Table 3 and FIG. 1 below.

TABLE 3

| Example formulas or comparable examples | The original active titers prior to freeze-thaw (Tu/ml) | The active titer at 37° C. for 48 h (Tu/ml) | Percent of the active titer at 37° C. for 48 h vs the original active titers (%) |
|---|---|---|---|
| Example formula 1 | $2 \times 10^{10}$ | $7.42 \times 10^9$ | 37.10 |
| Example formula 2 | $5.4 \times 10^7$ | $2.38 \times 10^7$ | 44.07 |
| Example formula 3 | $2 \times 10^6$ | $7.40 \times 10^5$ | 37.00 |
| Example formula 4 | $5 \times 10^6$ | $1.88 \times 10^6$ | 37.60 |
| Example formula 4 | $2 \times 10^6$ | $7.20 \times 10^5$ | 36.00 |
| Example formula 6 | $5.4 \times 10^7$ | $2.15 \times 10^7$ | 39.81 |
| Example formula 7 | $5 \times 10^8$ | $1.85 \times 10^8$ | 37.00 |
| Example formula 8 | $5 \times 10^6$ | $1.80 \times 10^6$ | 36.00 |
| Example formula 9 | $5.4 \times 10^7$ | $2.01 \times 10^7$ | 37.22 |
| Example formula 10 | $5 \times 10^6$ | $1.85 \times 10^6$ | 37.00 |
| Example formula 11 | $2 \times 10^6$ | $7.34 \times 10^5$ | 36.70 |
| Example formula 12 | $5 \times 10^6$ | $1.84 \times 10^6$ | 36.80 |
| Example formula 13 | $5 \times 10^6$ | $1.79 \times 10^6$ | 35.80 |
| Comparable example 1 | $5.4 \times 10^7$ | $1.00 \times 10^7$ | 18.52 |
| Comparable example 2 | $5.4 \times 10^7$ | $1.58 \times 10^7$ | 29.26 |
| Comparable example 3 | $5.4 \times 10^7$ | $7.20 \times 10^6$ | 13.33 |
| Comparable example 4 | $5.4 \times 10^7$ | $3.56 \times 10^6$ | 6.59 |

It can be seen form Table 3 that the stabilities of the Example formulas are better than the stabilities of the Comparable example formulas. Meanwhile, the Formulas of Example formula 2 and 6 is simple and have a stability much better than those of other Example formulas.

(2) Effect of Different Recombinant Lentiviral Vector Preparations on the Stability of the Recombination Lentivirus at 25° C.

Figure 2:
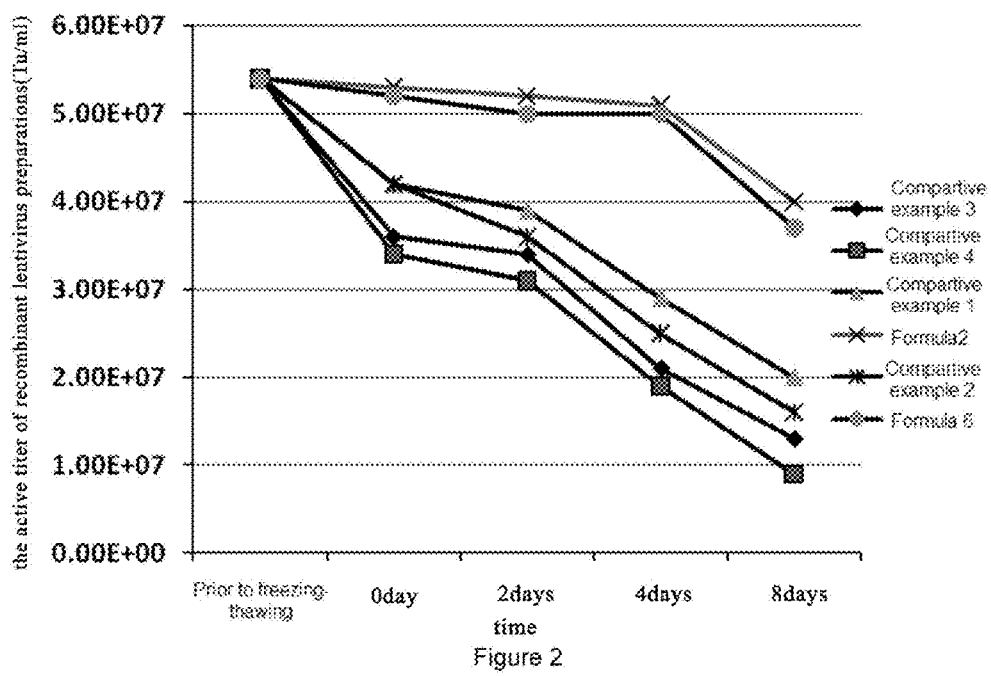
FIG. 2 represents the curves of the stabilities of Formulas 2, 6 and Comparable examples 1-4 at 25° C.

The recombinant lentiviral vector preparations formulated in Examples 1-13 and Comparable examples 1-4 were taken out from the storage circumstance of −80° C. and immediately placed into a water bath of 25° C. The corresponding samples were placed at different time points (8 d, 4 d, 2 d, 0 h). All of the samples was subjected to the active titer determination at the same time. The Determination titer of the viral particles was performed according to the method in the preparation examples. The results were shown in Table 4 and FIG. 2 below.

TABLE 4

| Example formulas or comparable examples | The original active titers prior to freeze-thaw (Tu/ml) | The active titers at 25° C. for 8 d (Tu/ml) | Percent of the active titers at 25° C. for 8 d vs the original active titers (%) |
|---|---|---|---|
| Example formula 1 | $2 \times 10^{10}$ | $1.25 \times 10^{10}$ | 62.50 |
| Example formula 2 | $5.4 \times 10^7$ | $4.00 \times 10^7$ | 74.07 |
| Example formula 3 | $2 \times 10^6$ | $1.27 \times 10^6$ | 63.50 |
| Example formula 4 | $5 \times 10^6$ | $3.21 \times 10^6$ | 64.20 |
| Example formula 4 | $2 \times 10^6$ | $1.26 \times 10^6$ | 63.00 |
| Example formula 6 | $5.4 \times 10^7$ | $3.7 \times 10^7$ | 68.52 |
| Example formula 7 | $5 \times 10^8$ | $3.17 \times 10^8$ | 63.40 |
| Example formula 8 | $5 \times 10^6$ | $3.10 \times 10^6$ | 62.00 |
| Example formula 9 | $5.4 \times 10^7$ | $3.44 \times 10^7$ | 63.70 |
| Example formula 10 | $5 \times 10^6$ | $3.14 \times 10^6$ | 62.80 |
| Example formula 11 | $2 \times 10^6$ | $1.21 \times 10^6$ | 60.50 |
| Example formula 12 | $5 \times 10^6$ | $2.98 \times 10^6$ | 59.60 |
| Example formula 13 | $5 \times 10^6$ | $2.89 \times 10^6$ | 57.80 |

TABLE 4-continued

| Example formulas or comparable examples | The original active titers prior to freeze-thaw (Tu/ml) | The active titers at 25° C. for 8 d (Tu/ml) | Percent of the active titers at 25° C. for 8 d vs the original active titers (%) |
|---|---|---|---|
| Comparable example 1 | $5.4 \times 10^7$ | $2.00 \times 10^7$ | 37.03 |
| Comparable example 2 | $5.4 \times 10^7$ | $1.60 \times 10^7$ | 29.63 |
| Comparable example 3 | $5.4 \times 10^7$ | $1.30 \times 10^7$ | 24.07 |
| Comparable example 4 | $5.4 \times 10^7$ | $9.00 \times 10^6$ | 16.67 |

It can be seen form Table 4 that the stabilities of the Example formulas are better than the stabilities of the Comparable example formulas. Meanwhile, the Formulas of Example formula 2 and 6 is simple and have a stability much better than those of other Example formulas.

(3) Effect of Different Recombinant Lentiviral Vector Preparations on the Stability of the Recombination Lentivirus at 4° C.

Figure 3:
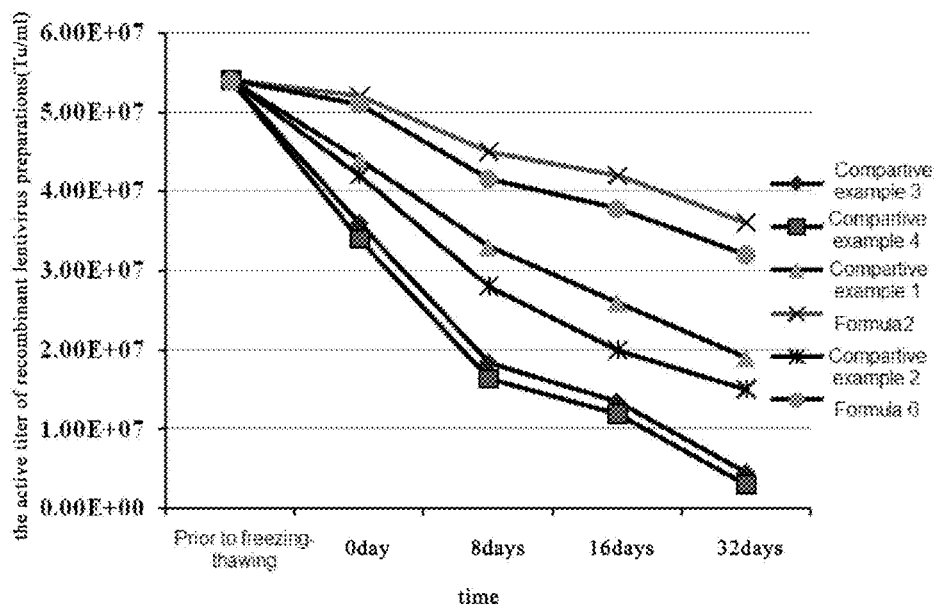
FIG. 3 represents the curves of the stabilities of Formulas 2, 6 and Comparable examples 1-4 at 4° C.

The recombinant lentiviral vector preparations formulated in Examples 1-13 and Comparable examples 1-4 were taken out from the storage circumstance of −80° C. and immediately placed into a water bath of 4° C. The corresponding samples were placed at different time points (32 d, 16 d, 8 d, 0 h). All of the samples was subjected to the active titer determination at the same time. The results were shown in Table 5 and FIG. 3 below.

TABLE 5

| Example formulas or comparable examples | The original active titers prior to freeze-thaw (Tu/ml) | the active titers at 4° C. for 32 d (Tu/ml) | Percent of the active titers at 4° C. for 32 d vs the original active titers (%) |
|---|---|---|---|
| Example formula 1 | $2 \times 10^{10}$ | $1.10 \times 10^{10}$ | 55.00 |
| Example formula 2 | $5.4 \times 10^7$ | $3.60 \times 10^7$ | 66.67 |
| Example formula 3 | $2 \times 10^6$ | $1.08 \times 10^6$ | 54.00 |
| Example formula 4 | $5 \times 10^6$ | $2.78 \times 10^6$ | 55.60 |
| Example formula 4 | $2 \times 10^6$ | $1.01 \times 10^6$ | 50.50 |
| Example formula 6 | $5.4 \times 10^7$ | $3.20 \times 10^7$ | 59.26 |
| Example formula 7 | $5 \times 10^8$ | $2.57 \times 10^8$ | 51.40 |
| Example formula 8 | $5 \times 10^6$ | $2.64 \times 10^6$ | 52.8 |
| Example formula 9 | $5.4 \times 10^7$ | $3.01 \times 10^7$ | 55.74 |
| Example formula 10 | $5 \times 10^6$ | $2.77 \times 10^6$ | 55.40 |
| Example formula 11 | $2 \times 10^6$ | $1.07 \times 10^6$ | 53.5 |
| Example formula 12 | $5 \times 10^6$ | $2.69 \times 10^6$ | 53.8 |
| Example formula 13 | $5 \times 10^6$ | $2.51 \times 10^6$ | 50.20 |
| Comparable example 1 | $5.4 \times 10^7$ | $1.9 \times 10^7$ | 35.19 |
| Comparable example 2 | $5.4 \times 10^7$ | $1.5 \times 10^7$ | 27.78 |
| Comparable example 3 | $5.4 \times 10^7$ | $4.5 \times 10^6$ | 8.33 |
| Comparable example 4 | $5.4 \times 10^7$ | $3.0 \times 10^6$ | 5.56 |

It can be seen form Table 5 that the stabilities of the Example formulas are better than the stabilities of the Comparable example formulas. Meanwhile, the Formulas of Example formula 2 and 6 is simple and have a stability much better than those of other Example formulas.

(4) Effect of Different Recombinant Lentiviral Vector Preparations on the Stability of the Recombination Lentivirus at −20° C.

Figure 4:
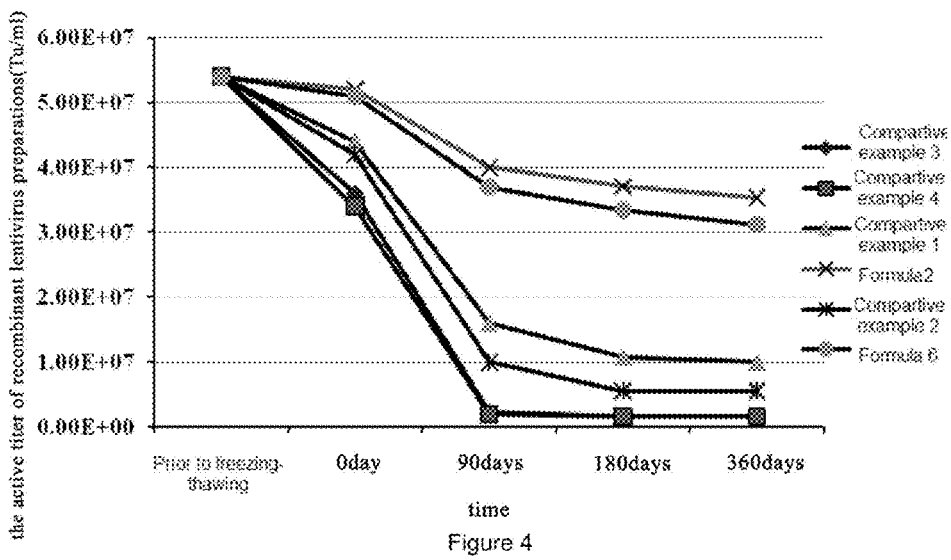
FIG. 4 represents the curves of the stabilities of Formulas 2, 6 and Comparable examples 1-4 at −20° C.

The recombinant lentiviral vector preparations formulated in Examples 1-13 and Comparable examples 1-4 were taken out from the storage circumstance of −80° C. and immediately stored at −20° C. The corresponding samples were placed at different time points (360 d, 180 d, 90 d, 0 h). All of the samples was subjected to the active titer determination at the same time. The results were shown in Table 6 and FIG. 4 below.

TABLE 6

| Example formulas or comparable examples | The original active titers prior to freezing-thawing (Tu/ml) | The active titers at −20° C. for 360 d (Tu/ml) | Percent of the active titers at −20° C. for 360 d vs the original active titers (%) |
|---|---|---|---|
| Example formula 1 | $2 \times 10^{10}$ | $1.08 \times 10^{10}$ | 54.00 |
| Example formula 2 | $5.4 \times 10^7$ | $3.54 \times 10^7$ | 65.56 |
| Example formula 3 | $2 \times 10^6$ | $1.07 \times 10^6$ | 53.5 |
| Example formula 4 | $5 \times 10^6$ | $2.77 \times 10^6$ | 55.40 |
| Example formula 4 | $2 \times 10^6$ | $9.84 \times 10^5$ | 49.20 |
| Example formula 6 | $5.4 \times 10^7$ | $3.12 \times 10^7$ | 57.78 |
| Example formula 7 | $5 \times 10^8$ | $2.55 \times 10^8$ | 51.00 |
| Example formula 8 | $5 \times 10^6$ | $2.54 \times 10^6$ | 50.78 |
| Example formula 9 | $5.4 \times 10^7$ | $3.00 \times 10^7$ | 55.56 |
| Example formula 10 | $5 \times 10^6$ | $2.72 \times 10^6$ | 54.40 |
| Example formula 11 | $2 \times 10^6$ | $1.05 \times 10^6$ | 52.50 |
| Example formula 12 | $5 \times 10^6$ | $2.65 \times 10^6$ | 53.00 |
| Example formula 13 | $5 \times 10^6$ | $2.49 \times 10^6$ | 49.80 |
| Comparable example 1 | $5.4 \times 10^7$ | $1.00 \times 10^7$ | 18.51 |
| Comparable example 2 | $5.4 \times 10^7$ | $5.55 \times 10^6$ | 10.28 |
| Comparable example 3 | $5.4 \times 10^7$ | $1.65 \times 10^6$ | 3.05 |
| Comparable example 4 | $5.4 \times 10^7$ | $1.60 \times 10^6$ | 2.96 |

It can be seen form Table 6 that the stabilities of the Example formulas are better than the stabilities of the Comparable example formulas. Meanwhile, the Formulas of Example formula 2 and 6 is simple and have a stability much better than those of other Example formulas.

(5) Effect of Different Recombinant Lentiviral Vector Preparations on the Stability of the Recombination Lentivirus at −80° C.

Figure 5:
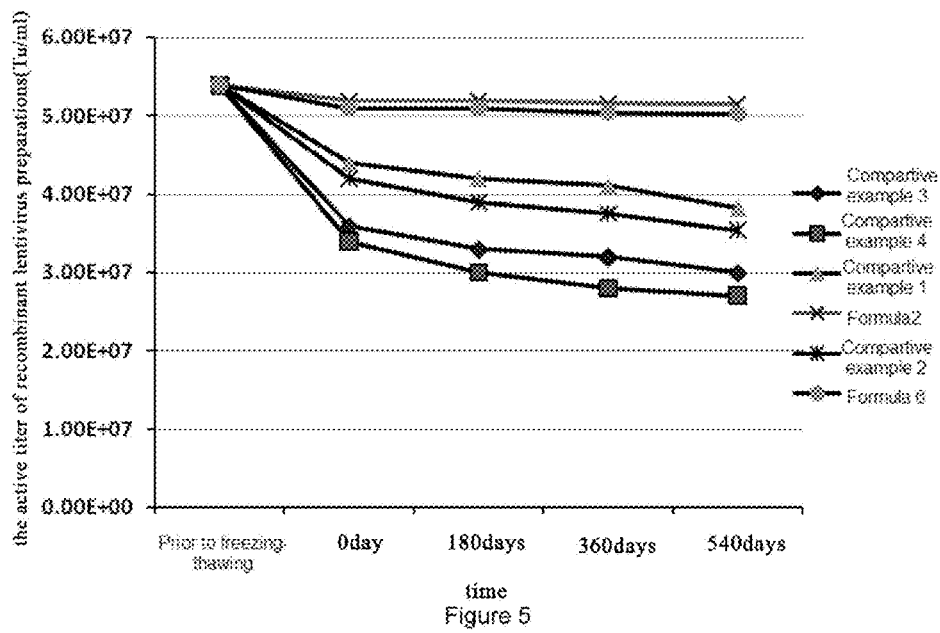
FIG. 5 represents the curves of the stabilities of Formulas 2, 6 and Comparable examples 1-4 at −80° C.

The recombinant lentiviral vector preparations formulated in Examples 1-13 and Comparable examples 1-4 were stored at −80° C. for 0 h, 180 d, 360 d, and 720 d. All of the preparations was subjected to the active titer determination at the same time, i.e. taken out from −80° C. to a water bath of 37° C., thawed and then placed on ice for of the active titer determination. The results were shown in Table 7 and FIG. 5 below.

TABLE 7

| Example formulas or comparable examples | The original active titers prior to freeze-thaw (Tu/ml) | The active titers at −80° C. for 720 d (Tu/ml) | Percent of the active titer at −80° C. for 720 d vs the original active titer (%) |
|---|---|---|---|
| Example formula 1 | $2 \times 10^{10}$ | $1.75 \times 10^{10}$ | 87.50 |
| Example formula 2 | $5.4 \times 10^{7}$ | $5.15 \times 10^{7}$ | 95.37 |
| Example formula 3 | $2 \times 10^{6}$ | $1.72 \times 10^{6}$ | 86.00 |
| Example formula 4 | $5 \times 10^{6}$ | $4.27 \times 10^{6}$ | 85.40 |
| Example formula 4 | $2 \times 10^{6}$ | $1.60 \times 10^{6}$ | 80.00 |
| Example formula 6 | $5.4 \times 10^{7}$ | $5.03 \times 10^{7}$ | 93.15 |
| Example formula 7 | $5 \times 10^{8}$ | $4.12 \times 10^{8}$ | 82.40 |
| Example formula 8 | $5 \times 10^{6}$ | $4.06 \times 10^{6}$ | 81.20 |
| Example formula 9 | $5.4 \times 10^{7}$ | $4.78 \times 10^{7}$ | 88.52 |
| Example formula 10 | $5 \times 10^{6}$ | $4.31 \times 10^{6}$ | 86.20 |
| Example formula 11 | $2 \times 10^{6}$ | $1.69 \times 10^{6}$ | 84.50 |
| Example formula 12 | $5 \times 10^{6}$ | $4.28 \times 10^{6}$ | 85.60 |
| Example formula 13 | $5 \times 10^{6}$ | $4.00 \times 10^{6}$ | 80.00 |
| Comparable example 1 | $5.4 \times 10^{7}$ | $3.82 \times 10^{7}$ | 70.74 |
| Comparable example 2 | $5.4 \times 10^{7}$ | $3.51 \times 10^{7}$ | 65.00 |
| Comparable example 3 | $5.4 \times 10^{7}$ | $3.00 \times 10^{7}$ | 55.56 |
| Comparable example 4 | $5.4 \times 10^{7}$ | $2.70 \times 10^{7}$ | 50.00 |

It can be seen form Table 7 that the stabilities of the Example formulas are better than the stabilities of the Comparable example formulas. Meanwhile, the Formulas of Example formula 2 and 6 is simple and have a stability much better than those of other Example formulas.

(6) Effect of the Repeated Freezing-Thawing on the Stabilities of the Different Recombinant Lentivirus Preparations.

Figure 6:
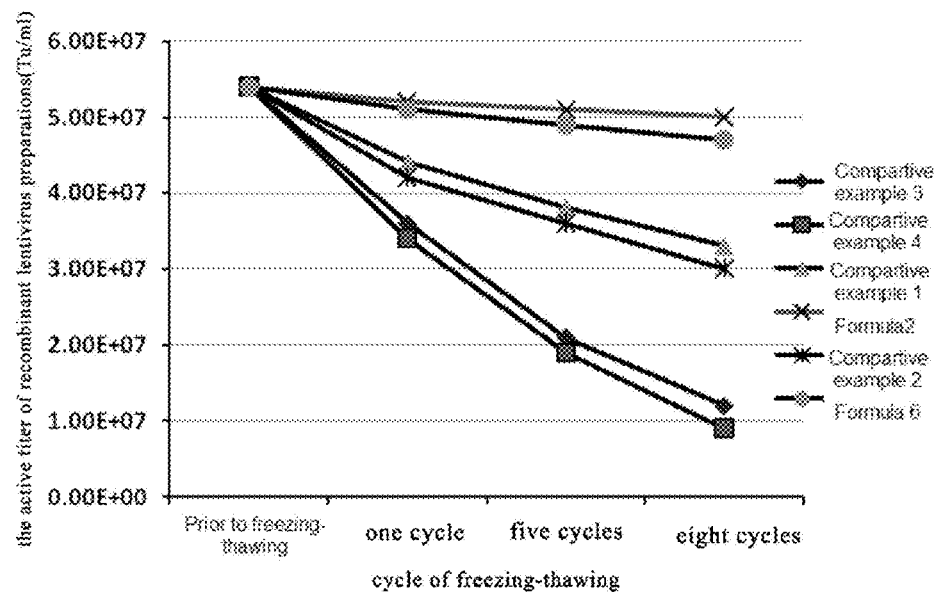
FIG. 6 represents the curves of the stabilities of Formulas 2, 6 and Comparable examples 1-4 under the condition of freeze-thaw cycles.

The recombinant lentiviral vector preparations formulated in Examples 1-13 and Comparable examples 1-4 were aliquoted sterilely. The titers of some of aliquots were immediately determined, known as the titers prior to freezing-thawing. Other aliquots were placed into liquid nitrogen for flash freezing and taken out after 10 min of flash freezing, and then placed in a water bath of 37° C. with shaking from time to time, and taken out from the water bath when the different preparations were observed to be full thawed. This was recorded as the first freezing-thawing. Again, these aliquots were placed immediately into liquid nitrogen for flash freezing and taken out after 10 min of flash freezing, and then placed in a water bath of 37° C. with shaking from time to time, and taken out from the water bath when the different preparations were observed to be full thawed. This was recorded as the second freezing-thawing. The freezing-thawing cycle was repeated subsequently up to five times and eight times. The titers of the samples prior to freezing-thawing, the samples undergoing freezing-thawing five times and the samples undergoing freezing-thawing eight times were determined. The results were shown in Table 8 and FIG. 6 below.

TABLE 8

| Example formulas or comparable examples | The original active titers prior to freeze-thaw (Tu/ml) | The active titers after eight cycles of freezing-thawing (Tu/ml) | Percent of the active titer after eight cycles of freezing-thawing vs the original active titers (%) |
|---|---|---|---|
| Example formula 1 | $2 \times 10^{10}$ | $1.66 \times 10^{10}$ | 83.00 |
| Example formula 2 | $5.4 \times 10^{7}$ | $5.00 \times 10^{7}$ | 92.59 |
| Example formula 3 | $2 \times 10^{6}$ | $1.62 \times 10^{6}$ | 81.00 |
| Example formula 4 | $5 \times 10^{6}$ | $4.00 \times 10^{6}$ | 80.00 |
| Example formula 4 | $2 \times 10^{6}$ | $1.60 \times 10^{6}$ | 74.50 |
| Example formula 6 | $5.4 \times 10^{7}$ | $4.70 \times 10^{7}$ | 87.04 |
| Example formula 7 | $5 \times 10^{8}$ | $3.92 \times 10^{8}$ | 78.40 |
| Example formula 8 | $5 \times 10^{6}$ | $3.84 \times 10^{6}$ | 76.80 |
| Example formula 9 | $5.4 \times 10^{7}$ | $4.48 \times 10^{7}$ | 82.96 |
| Example formula 10 | $5 \times 10^{6}$ | $4.10 \times 10^{6}$ | 82.00 |
| Example formula 11 | $2 \times 10^{6}$ | $1.59 \times 10^{6}$ | 79.50 |
| Example formula 12 | $5 \times 10^{6}$ | $4.04 \times 10^{6}$ | 80.08 |
| Example formula 13 | $5 \times 10^{6}$ | $3.68 \times 10^{6}$ | 73.60 |
| Comparable example 1 | $5.4 \times 10^{7}$ | $3.30 \times 10^{7}$ | 61.11 |
| Comparable example 2 | $5.4 \times 10^{7}$ | $3.00 \times 10^{7}$ | 55.56 |
| Comparable example 3 | $5.4 \times 10^{7}$ | $1.20 \times 10^{7}$ | 22.22 |
| Comparable example 4 | $5.4 \times 10^{7}$ | $9.00 \times 10^{6}$ | 16.67 |

It can be seen form Table 5 that the stabilities of the Example formulas are better than the stabilities of the Comparable example formulas. Meanwhile, the Formulas of Example formula 2 and 6 is simple and have a stability much better than those of other Example formulas.

What is claimed is:

1. A storage stable recombinant lentiviral vector preparation, wherein said preparation comprises:
   a) an effective dose of a recombinant lentiviral vector, wherein said recombinant lentiviral vector is a simian immunodeficiency virus (SIV) vector or a human immunodeficiency virus (HIV) vector and wherein said SIV or HIV vector is coated with vesicular stomatitis virus G protein;
   b) a histidine hydrochloride buffer at a concentration of 1-50 mM for maintaining recombinant lentiviral vector stability and keeping a pH value of said preparation in the range of 6.0-8.0; and
   c) a sugar selected from the group consisting of glucose, fructose, trehalose, and sucrose.

2. The recombinant lentiviral vector preparation according to claim 1, wherein said recombinant lentiviral vector further comprises any one sequence selected from the group consisting of the central polypurine tract, the post-transcriptional regulatory element of woodchuck hepatitis virus, the constitutive transport element, the RNA transport element, and the accessory gene Vpx of HIV-1 virus.

3. The recombinant lentiviral vector preparation according to claim 1, wherein said recombinant lentiviral vector is said recombinant HIV.

4. The recombinant lentiviral vector preparation according to claim 1, wherein said recombinant lentiviral vector is said recombinant SIV vector, and said SIV vector comprises a human pigment epithelium-derived factor gene or small RNA fragments interfering with replication of HIV virus.

5. The recombinant lentiviral vector preparation according to claim 1, wherein dosage of said recombinant lentiviral vector is $2 \times 10^6$-$2 \times 10^{10}$ Tu/ml.

6. The recombinant lentiviral vector preparation according to claim 5, wherein the dosage of said recombinant lentiviral vector is $5 \times 10^6$-$2 \times 10^{10}$ Tu/ml.

7. The recombinant lentiviral vector preparation according to claim 1, wherein the pH value of said preparation is in the range of 6.5-7.4.

8. The recombinant lentiviral vector preparation according to claim 7, wherein the pH value of said preparation is 7.2.

9. The recombinant lentiviral vector preparation according to claim 1, wherein the molar concentration of histidine hydrochloride is in the range of 10-50 mmol/L.

10. The recombinant lentiviral vector preparation according to claim 9, wherein the molar concentration of histidine hydrochloride is 10 mmol/L.

11. The recombinant lentiviral vector preparation according to claim 1, wherein said sugar is trehalose.

12. The recombinant lentiviral vector preparation according to claim 1, wherein said sugar is in the range of 2-10% by percent weight in volume, on the basis of the recombinant lentiviral vector preparation.

13. The recombinant lentiviral vector preparation according to claim 12, wherein said sugar is in the range of 5-10% by percent weight in volume, on the basis of the recombinant lentiviral vector preparation.

14. The recombinant lentiviral vector preparation according to claim 13, wherein said sugar is 10% or 5% by percent weight in volume, on the basis of the recombinant lentiviral vector preparation.

15. The recombinant lentiviral vector preparation according to claim 1, wherein said recombinant lentiviral vector preparation comprises:
   a) a recombinant SIV vector comprising the human pigment epithelium-derived factor gene at a dosage of $5 \times 10^6$-$5 \times 10^8$ Tu/ml;
   b) 10 mmol/L of the histidine hydrochloride buffer for keeping the pH value of said preparation in the range of 7.2; and
   c) trehalose at a concentration of 10% by percent weight in volume on the basis of the recombinant lentiviral vector preparation.

16. The recombinant lentiviral vector preparation according to claim 1, wherein said recombinant lentiviral vector preparation comprises:
   a) a recombinant SIV vector comprising the human pigment epithelium-derived factor gene at a dosage of $5 \times 10^6$-$5 \times 10^8$ Tu/ml;
   b) 10 mmol/L of the histidine hydrochloride buffer for keeping the pH value of said preparation in the range of 7.2; and
   c) glucose at a concentration of 5% by percent weight in volume on the basis of the recombinant lentiviral vector preparation.

17. The recombinant lentiviral vector preparation according to claim 1, wherein said recombinant lentiviral vector preparation further comprises an isosmotic agent, and the osmolality of the recombinant lentiviral vector preparation comprising the isosmotic agent is 0.6%-2.7% of sodium chloride solution.

18. The recombinant lentiviral vector preparation according to claim 17, wherein said isosmotic agent is NaCl.

19. The recombinant lentiviral vector preparation according to claim 1, wherein said recombinant lentiviral vector preparation further comprises 2 mmol/L of $MgCl_2$.

20. The recombinant lentiviral vector preparation according to claim 1, wherein said recombinant lentiviral vector preparation further comprises a surface active agent at a concentration of 0.005-0.015% by percent weight in volume on the basis of the recombinant lentiviral vector preparation.

21. The recombinant lentiviral vector preparation according to claim 20, wherein said surface active agent is Tween-20, Tween-80, or polyoxyethylene hydrogenated castor oil RH-40.

22. The recombinant lentiviral vector preparation according to claim 1, wherein said recombinant lentiviral vector preparation further comprises a preserving agent at a final concentration of 0.001-1.0% by percent weight in volume on the basis of the recombinant lentiviral vector preparation.

23. The recombinant lentiviral vector preparation according to claim 22, wherein said preserving agent is phenol at a concentration of 0.5-1.0% by percent weight in volume on the basis of aqueous solution of phenol.

24. The recombinant lentiviral vector preparation according to claim 1, wherein said recombinant lentiviral vector preparation further comprises at least one of mannitol or glycerol.

25. The recombinant lentiviral vector preparation according to claim 1, wherein said recombinant lentiviral vector preparation further comprises at least one of human serum albumin or bovine serum albumin.

26. The recombinant lentiviral vector preparation according to claim 1, wherein said recombinant lentiviral vector preparation further comprises at least one of histidine, glycine, alanine, or lysine.

27. The recombinant lentiviral vector preparation according to claim 1, wherein said recombinant lentiviral vector preparation further comprises an antioxidant at a concentration of 0.01-1.0% by percent weight in volume on the basis of the recombinant lentiviral vector preparation.

28. The recombinant lentiviral vector preparation according to claim 27, wherein said antioxidant is (a) sodium sulfite or sodium bisulphite at a concentration of 0.1-0.2% by percent weight in volume on the basis of the recombinant lentiviral vector preparation, or (b) sodium thiosulfate at a concentration of 0.1% by percent weight in volume on the basis of the recombinant lentiviral vector preparation.

29. The recombinant lentiviral vector preparation according to claim 1, wherein said recombinant lentiviral vector preparation further comprises (a) dimethyl sulphoxide at a concentration of 5-50% by percent weight in volume or (b) polyprene at a concentration of 2-20% by percent weight in volume, on the basis of the recombinant lentiviral vector preparation.

30. The recombinant lentiviral vector preparation according to claim 1, wherein said recombinant lentiviral vector preparation further comprises a cytokine required for growth of hematopoietic stem cells or peripheral blood monocytes, at a concentration of 5-10% by percent weight in volume on the basis of the recombinant lentiviral vector preparation.

* * * * *